United States Patent
Krulevitch et al.

(10) Patent No.: US 6,319,474 B1
(45) Date of Patent: Nov. 20, 2001

(54) MICROFABRICATED INSTRUMENT FOR TISSUE BIOPSY AND ANALYSIS

(75) Inventors: Peter A. Krulevitch, Pleasanton; Abraham P. Lee, Walnut Creek; M. Allen Northrup, Berkeley; William J. Benett, Livermore, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/327,401

(22) Filed: Jun. 7, 1999

Related U.S. Application Data

(62) Division of application No. 08/895,786, filed on Jul. 17, 1997, now Pat. No. 5,985,217.

(51) Int. Cl.$^7$ ...................................................... B01L 11/00
(52) U.S. Cl. ................... 422/99; 30/278; 30/289; 83/167; 83/856; 83/915.5; 422/82.05; 422/102; 600/564; 606/172
(58) Field of Search ....................... 422/99, 102, 82.05; 600/564, 570; 606/172; 436/174, 177, 176; 83/167, 440, 520, 856, 915.5; 30/278, 280, 289, 294

(56) References Cited

U.S. PATENT DOCUMENTS 4,271,740 * 6/1981 Yamazaki et al. .
5,842,387 * 12/1998 Marcus et al. .
6,003,419 * 12/1999 Irita et al. .

* cited by examiner

*Primary Examiner*—Jan Ludlow
(74) *Attorney, Agent, or Firm*—L. E. Carnahan; Alan H. Thompson

(57) ABSTRACT

A microfabricated biopsy/histology instrument which has several advantages over the conventional procedures, including minimal specimen handling, smooth cutting edges with atomic sharpness capable of slicing very thin specimens (approximately 2 μm or greater), micro-liter volumes of chemicals for treating the specimens, low cost, disposable, fabrication process which renders sterile parts, and ease of use. The cutter is a "cheese-grater" style design comprising a block or substrate of silicon and which uses anisotropic etching of the silicon to form extremely sharp and precise cutting edges. As a specimen is cut, it passes through the silicon cutter and lies flat on a piece of glass which is bonded to the cutter. Microchannels are etched into the glass or silicon substrates for delivering small volumes of chemicals for treating the specimen. After treatment, the specimens can be examined through the glass substrate.

19 Claims, 3 Drawing Sheets

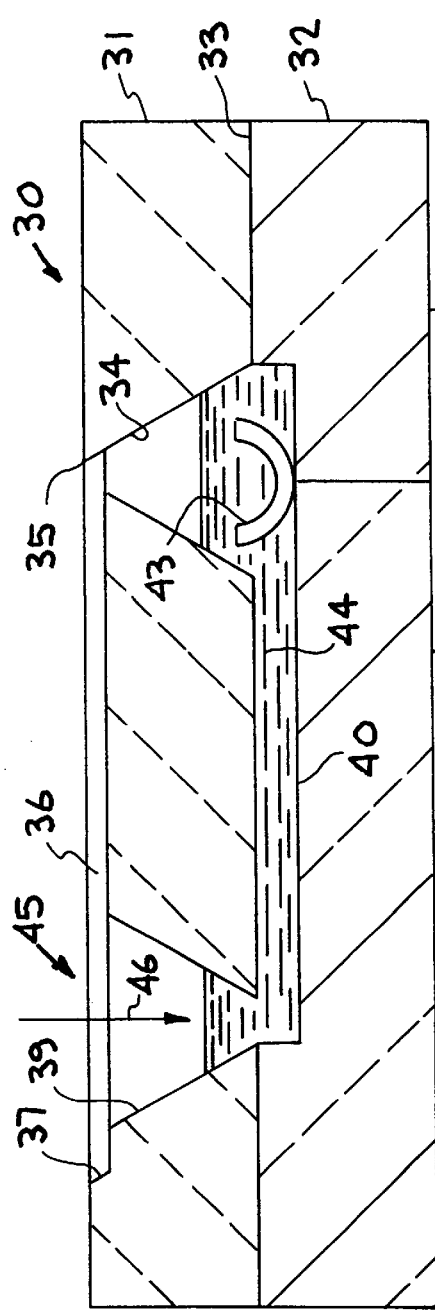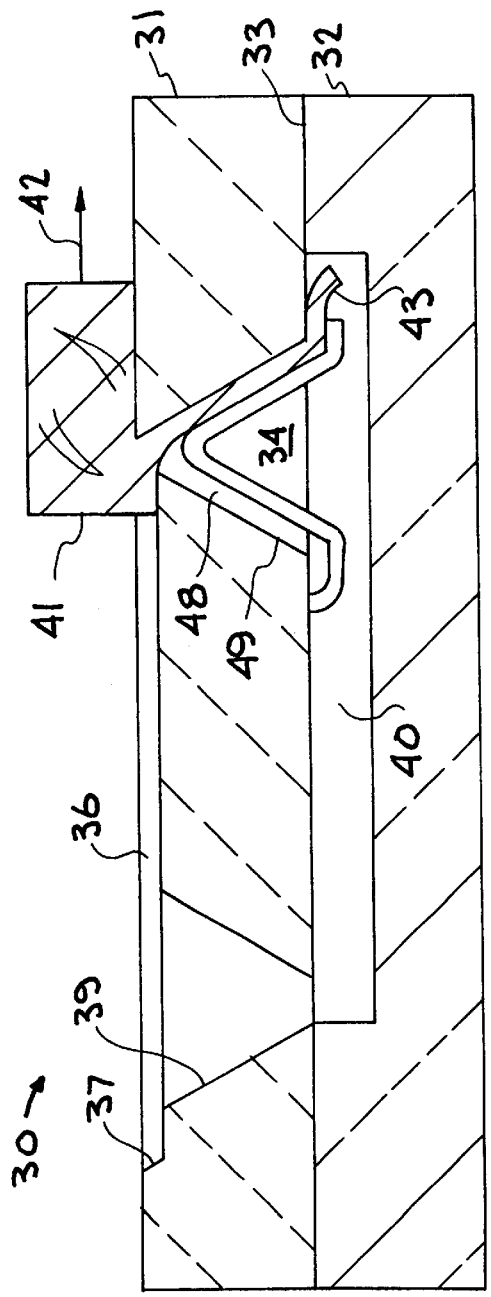

MICROFABRICATED INSTRUMENT FOR TISSUE BIOPSY AND ANALYSIS

This application is a divisional of application Ser. No. 08/895,786, filed Jul. 17, 1997, now U.S. Pat. No. 5,985,217.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to preparing tissue samples for pathological study, particularly to a microfabricated instrument for tissue biopsy and analysis, and more particularly to a microfabricated biopsy/histology system using a combined tissue cutter and specimen treatment chamber, thus minimizing specimen handling.

The process of preparing tissue samples for pathological study, known as histology, requires skill and experience. The current process used for preparing samples for histological analysis is labor intensive, somewhat of an art form, and requires expensive equipment and large quantities of chemicals. In the traditional process, a piece of tissue is embedded in paraffin wax, and thin ribbons are sliced off using a microtome, then mounted onto glass slides, treated with chemicals, and viewed with a microscope. Large quantities of chemicals are required to fix, dehydrate, and stain the tissue. In addition, the large tissue samples removed from a patient causes substantial discomfort.

Recently, micro-biopsy tools have been developed to enable removing only a small amount of tissue or other material in a minimally invasive manner, and reduce risks, costs, injury, and patient discomfort associated with traditional biopsy procedures. Such micro-biopsy tools are described and claimed in copending U.S. application Ser. No. 08/887,780 filed Jul. 3, 1997 entitled "Micro-biopsy/Precision Cutting Devices", now U.S. Pat. No. 5,928,161 assigned to the same assignee. These micro-biopsy tools are formed from silicon and anisotropic etching of silicon, resulting in extremely sharp edges, ideally suited for slicing soft tissues.

The present invention significantly simplifies specimen slicing and subsequent chemical treatment, and combines these operations into one complete histology instrument. The sample is sliced to a precise thickness with a micromachined silicon cutter, trapped in a chamber such that the sample lies flat against a glass surface, treated with appropriate chemicals, and viewed through the glass, all without directly handling the specimen after it has been sliced. The system of this invention may be used to slice and process fresh tissue samples or samples embedded in paraffin wax. The system of this invention has three components: a cutter for directly performing a microbiopsy or slicing a thin section from previously biopsied tissue, and specimen chamber for capturing, treating, and viewing the thin cut section, and flow channels for exposing the specimen to a variety of chemicals. The cutter is formed by anisotropic etching of silicon and enables slicing very thin specimens (about 2 μm or greater).

SUMMARY OF THE INVENTION

It is an object of the present invention to provide a microfabricated instrument for tissue biopsy and analysis.

A further object of the invention is to provide a microfabricated instrument for acquiring specimens for DNA analysis.

A further object of the invention is to provide a microfabricated biopsy/histology system.

Another object of the invention is to provide a biopsy/histology system, which combines sample cutting, sample analysis, and sample viewing in a single instrument thus minimizing sample handling.

Another object of the invention is to provide an instrument induding a silicon cutter having a cutting edge formed by anisotropic etching of the silicon.

Another object of the invention is to provide a biopsy/histology instrument that utilizes a silicon member bonded to a glass member, with the silicon member including a specimen tissue cutter and the glass member induding microchannels for small volumes of chemicals for treating cut tissue specimens.

Other objects and advantages will become apparent from the following description and accompanying drawings. The present invention is a microfabricated biopsy/histology instrument which has several advantages over the conventional procedures, including minimal specimen handling, smooth cutting edges with atomic sharpness capable of slicing very thin specimens (approximately 2 μm or greater), microliter volumes of chemicals for treating the specimens, low cost and thus disposable, and ease of use. The system of this invention has three components: 1) a cutter for directly performing a microbiopsy or slicing a thin section from previously biopsied tissue, 2) a specimen chamber for capturing, treating, and viewing the thin section, and 3) flow channels for exposing the specimen to a variety of chemicals. The system also includes means for causing the cut specimen to lie flat in the specimen chamber.

BRIEF DESCRIPTION OF THE DRAWINGS

The accompanying drawings, which are incorporated into and form a part of the discourse, illustrate embodiments of the invention and, together with the description, serve to explain the principles of the invention.

FIGS. 3A–3C illustrate in cross-section an embodiment of a microfabricated biopsy/histology instrument using a cutter section similar to that of FIG. 2, and illustrating the chemical channels and the cutting/analysis procedure.

FIG. 4 is a view similar to FIG. 3A but incorporating means for insuring that the cut specimen lies flat in the chemical treatment channel.

DETAILED DESCRIPTION OF THE INVENTION

The present invention involves a microfabricated instrument for tissue biopsy and analysis. The microfabricated biopsy/histology system or instrument has several advantages over the conventional procedures, including minimal specimen handling, smooth cutting edges with atomic sharpness capable of slicing very thin specimens (about 2 μm or greater), micro-liter volumes of chemicals for treating the specimens, low cost, disposability, fabrication process which renders sterile parts, and ease of use. The instrument has three components: a cutter, a specimen chamber, and flow channels for chemicals. The cutter is of a "cheese-grater" type which uses anisotropic etching of silicon to form extremely sharp and precise cutting edges. As the specimen is cut, it passes through the silicon cutter to a specimen chamber and lies flat on a piece of glass bonded to the silicon cutter. Microchannels are etched into the glass substrate and/or the silicon substrate forming the cutter, for delivering small volumes of chemicals for treating the specimen. Means are provided to insure that the cut specimen lies flat on the specimen chamber. After treatment, the specimens can be examined through the glass side of the instrument. By use of this instrument minimal specimen handling is needed.

The silicon cutter of the instrument is constructed by bulk micromachining of single crystal silicon using anisotropic etchants, such as potassium hydroxide (KOH), which results in precisely defined {100} silicon and {111} silicon planar surfaces which meet at a 54.7 degree angle with near atomic sharpness, forming edges which are ideal for soft tissue cutting. Alternatively, {110} oriented silicon can be used, providing a 35.3° angle with the {111} plane. In addition, silicon has excellent mechanical properties, including high fracture strength, and stiffness almost as high as steel. The cuter can be designed to take slices between 2 and 500 $\mu$m in thickness. A silicon micromachining fabrication approach has the following additional advantages: low cost per cutter particularly for volumes in the tens of thousands or greater due to batch fabrication, and a highly controlled cleanroom environment results in as-fabricated sterile devices, and parts are disposable.

Figure 1:
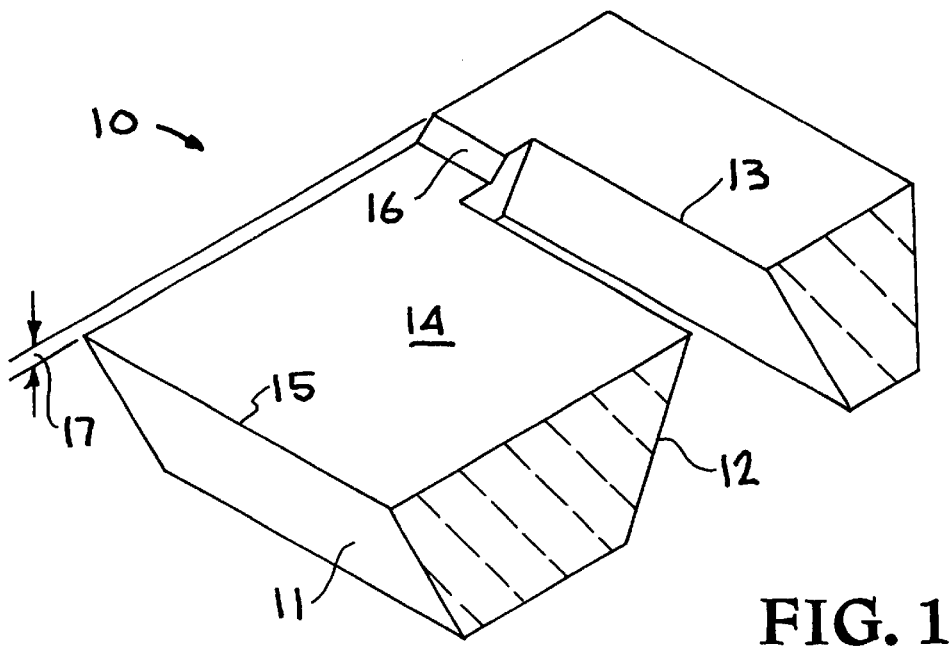
FIG. 1 is a three-dimensional cross-sectional view of an embodiment of a silicon micromachined tissue cutter made in accordance with the present invention.
Figure 2:
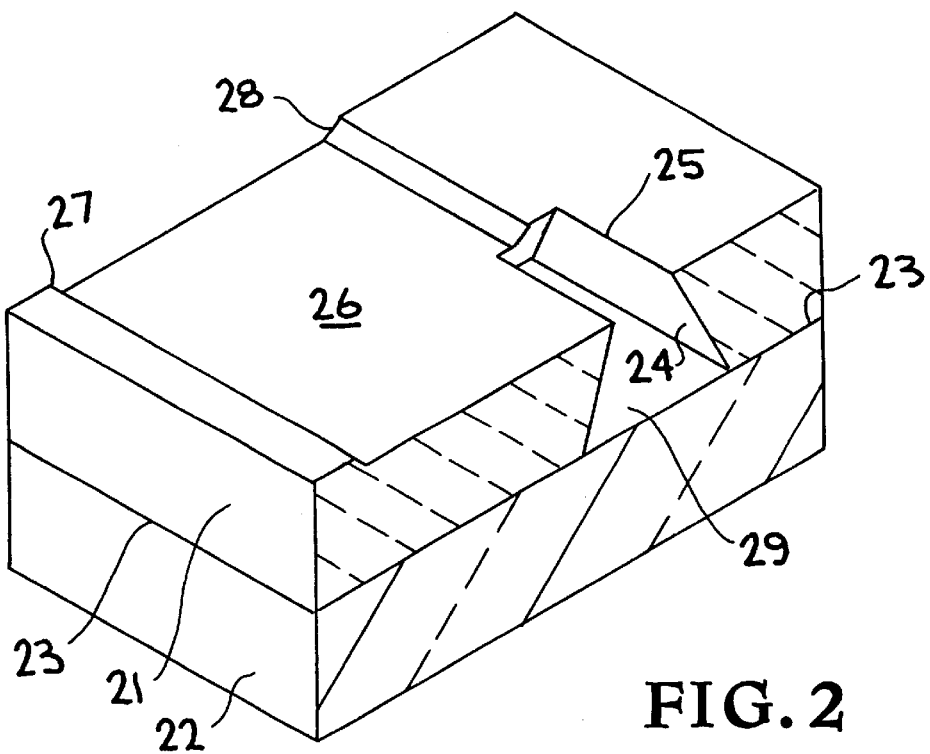
FIG. 2 is a cross-sectional three-dimensional view of the cutter section of a microfabricated biopsy/histology instrument made in accordance with the present invention and utilizing a tissue cutter generally similar to that of FIG. 1, but including a sample trough.

Experimental verification of the invention first involved establishing an effective silicon cutter design, with a final design being illustrated in FIG. 1, which is a modification of the design of the cutter illustrated in FIG. 2. The difference is the elimination of the sample or specimen trough of the FIG. 2 embodiment in which tissue to be sampled is located prior to cutting by the associated sharp leading or cutting edge of the scion cutter. The FIG. 1 embodiment utilizes two spaced cutting edges, a pre-cut edge and a final cut edge.

The experimental test embodiment illustrated in cross-section in FIG. 1 comprises a cutting device 10 composed of a silicon body or substrate 11 having a tapered opening or slot 12 which terminates in a sharp leading or cutting edge 13 and a cut-away section 14 having a leading or pre-cut edge 15 and a trailing tapered edge 16 which is located adjacent to the sharp leading edge 13 of tapered opening or slot 12. The depth of the cut-away section 14 indicated at 17 was designed for cutting specimens 10–15 $\mu$m thick from paraffin wax. The tapered opening 12 defines a collection pit and is shaped as a rectangular pyramid. A fixture was used to slide the sample across the cutter device 10, which took a reference cut at the leading or pre-cut edge 15, then cut the thin slice at the sharp leading edge 13. The slice thickness is determined by etch depth 17, as shown in FIG. 1. The first experimental cutter devices constructed to verify the device were fabricated from {100} silicon, which produced a cutting angle of 54.7 degrees and resulted in bunching of the sample at the thin cut section (adjacent sharp leading edge 13). Switching to {110} silicon, cutters were produced with 35 degree cutting edges which substantially reduced the bunching problem. Due to the bunching problem, initial specimen thickness ranged from 12–18 $\mu$m with a cut depth of 4–7 $\mu$m. Tests established that cutter devices with a blade separation of 750 $\mu$m were too fragile, while a separation of 520 $\mu$m resulted in large variations in sample thickness. These tests established that a 200–300 $\mu$m separation appeared to be optimum.

Transmission electron microscopy was used to evaluate the structure of the micromachined silicon cutter devices, which revealed previously unknown defects on the {100} silicon surfaces. The 100–200 m defects, which appeared on {100} surfaces only, not on the {110} silicon surfaces, had a structure resembling porous silicon, and are formed when the masking silicon nitride film is stripped from the silicon surface in hydrofluoric acid.

As a result of the verification testing a preferred cutter device configuration was determined, and such is illustrated in FIG. 1. The primary, difference in the FIG. 1 preferred cutter device is in the elimination of the sample trough or cut-away section on the upper surface and a sharp leading edge, shown at 15.

Figure 3A:
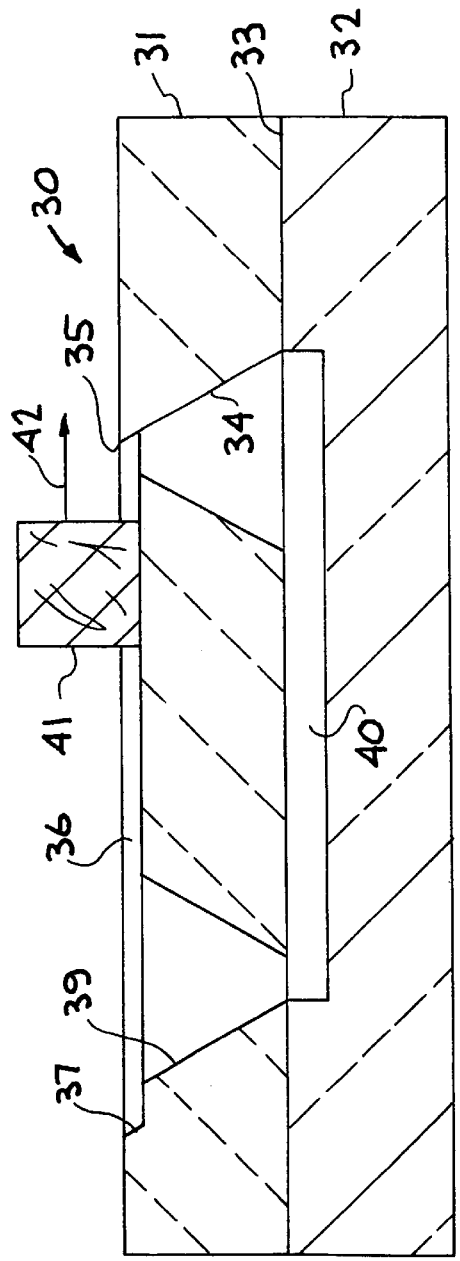
Figure 3B:
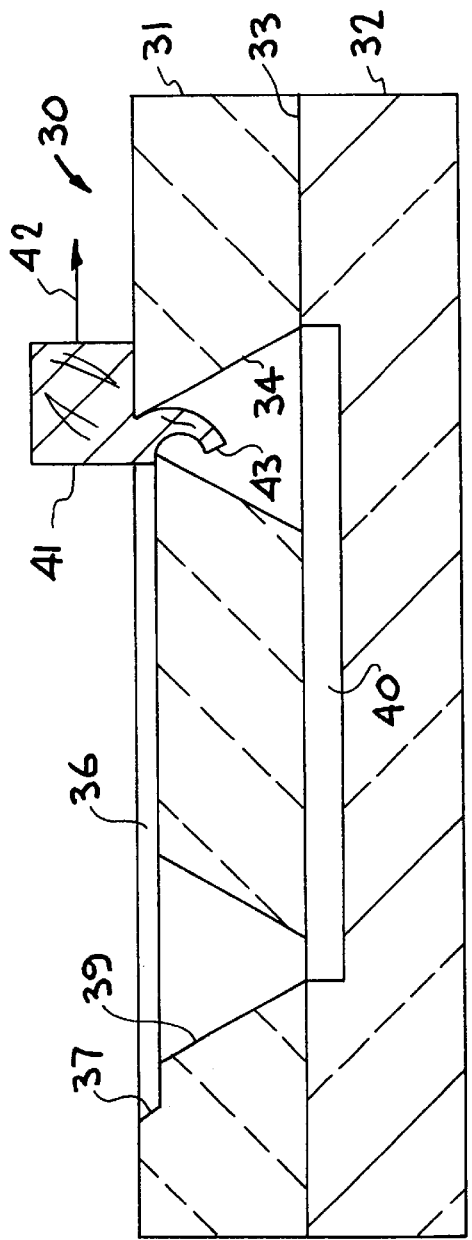

FIG. 2 shows a cross-sectional view of a silicon micromachined cutter device bonded to a glass substrate, and which as fully illustrated in FIGS. 3A–3C forms another embodiment of a biopsy/histology instrument or system of the present invention, but which utilizes a sample trough.

The cutter device, as shown in FIG. 2 has been fabricated using an operational sequence set forth generally as follows;

1. Deposit a masking layer of silicon nitride on the silicon wafer, substrate, or block.

2. Form a window in the masking layer on the back side (lower surface as shown) of the wafer for the opening or slot which will form the cutter and a collection pit.

3. Etch the cutter opening or slot through the wafer in KOH, stopping on the silicon nitride layer.

4. Form a window in the masking layer on the front side (upper surface as shown) of the substrate for the indentation which defines the depth of cut (the sample trough) or cutting edge. The mask layer on the front side for this step must be aligned to the pattern on the back side of the wafer to assure proper termination of the indentation (trough) with respect to the opening or slot.

5. Using a timed etch in KOH to define the indentation (trough) depth.

6. Strip the remaining silicon nitride masking layer.

Where the cutter device of FIG. 2 is to be incorporated into the instrument of FIGS. 3A–3C, an additional opening or slot is formed at an opposite end of the indentation (trough). Then a piece (substrate) of glass is anodically bonded to the backside of the cutter wafer, forming a specimen chamber or cavity, as shown in FIG. 2. Also, the upper surface of the silicon member can be formed as in FIG. 1 to remove the sample trough.

Prior to bonding the silicon cutter to the glass substrate, one or more micro-channels are formed on the upper surface of the glass substrate and/or on the back side (lower surface) of the silicon wafer or substrate, as described hereinafter with respect to FIGS. 3A–3C.

Referring now to the cutter device illustrated FIG. 2, this embodiment, generally indicated at 20, comprises a silicon wafer, substrate, or member 21 and a glass substrate or member 22 bonded to silicon member 21 as indicated at 23, such as by an anodic bonding technique. Silicon member 21 is provided with a tapered opening or slot 24 which extends through member 21 and terminates on one side in a sharp cutting edge 25. Member 21 also includes an indentation or cut-away through section 26 having tapered end surfaces 27 and 28. The opening or slot 24 of silicon member 21 forms with an upper surface of glass substrate or member 22 a specimen chamber or collection pit 29, as illustrated in detail in FIGS. 3A–3C.

Referring now to FIGS. 3A–3C an embodiment of a biopsy/histology instrument is shown utilizing a cutter section as illustrated in FIG. 2. The instrument generally indicated at 30 comprises a silicon member or substrate 31 and a glass member or substrate 32 bonded together at 33. Silicon member 31 includes a tapered opening or slot 34 terminating at the upper surface of members 31 in a sharp cutting edge 35, and a cut-away section or indentation 36 having tapered end surfaces 37 (only one shown). The cut-away section 36 may extend across to upper surface of member 31 as in the FIG. 2 embodiment or only partially across the upper surface. Member 31 includes a second tapered opening 39 which extends from cutaway section 36 through member 31 but tapers in an opposite direction from the taper of opening or slot 34. The glass member or substrate 32 includes at least one cut-away, groove or microchannel 40 which extends from opening 34 to opening 39 of silicon member 31. While not shown, and depending on the size of the instrument and the desired application thereof, the cut-away or groove 40 may extend the width of the opening or slot 34 or less than that width, or multiple grooves or microchannels 40 can be formed in glass member 32.

In operation of the instrument of FIGS. 3A–3C, a tissue sample 41 is directed along cut-away section 36, which forms a sample trough, as indicated by arrow 42 causing a slice or specimen 43 of tissue sample 41 to be cut by sharp cutting edge 35, which drops through opening 34 into the groove or microchannel 40 in glass member 32 for treatment by a chemical 44 in groove 40 which is directed into groove 40 via opening 39, which defines a chemical input port 45, as indicated by arrow 46. Optical analysis as indicated by arrow 47, of the specimen 43 is accomplished by viewing the specimen through the glass member 32. The cut-away section 36 can be extended to the end of substrate or member 31 and the edge of member 31 tapered as in the FIG. 1 embodiment whereby two spaced cutting edges are provided, as described above with respect to FIG. 1.

It is preferable that the specimen 43 lies flat in groove 40, but in many instances it is curved as shown in FIG. 3C. To prevent curvature of the sample or specimen 43 and insurance that it lies flat in groove 40 a shaped polysilicon member 47 may be positioned or formed in opening 34, as shown in FIG. 4, to form a space 48 adjacent a surface 48 of member 31 through which the same passes into groove 40', which has been extended in length past the openings 34 and 39, as seen by a comparison of FIG. 4, with FIGS. 3A–3C. However, the groove 40' need only extend past opening 34 to enable of the specimen 43 therein when the polysilicon member 43 is positioned or formed in opening or slot 34.

While not shown, the instrument of FIGS. 3A–3C may be incorporated into a system utilizing existing microvalves and micropumps. If microchannels, microvalves, and micropumps are to be included, they can be fabricated on the same silicon wafer as the cutter, or may be included with the glass substrate or on a separate silicon wafer which is bonded to the cutter wafer. Such micro-devices can be produced by known techniques. In addition, thin films of material such as diamond or silicon carbide can be deposited or grown on selected surfaces of the cutter, particularly the cutting edge, to increase the cutter hardness.

By way of example, the instrument of FIGS. 3A–3C may be constructed with the silicon cutter substrate 31 having a length of 10 to 50 mm, width of 10 to 50 mm, and thickness of 0.1 to 1.0 mm; the glass substrate 32 has a thickness of 0.2 to 2.0 mm and a length and width which corresponds to the dimensions of the silicon substrate 31. The opening or slot 34 has a taper of about 35.3° for {110} silicon or 54.7° for {100} silicon, for example, with the upper area (adjacent the cutter edge 35) preferably having a width of 200–300 $\mu$m for thin slices or specimens (about 2–5 $\mu$m) but may be made wider for large slices (up to 500 $\mu$m). The indentation or cut-away 36 may have a length of 1 to 30 mm, width of 5 to 40 mm, and a depth of 2–500 $\mu$m depending on the thickness of the slices to be made. The opening 39 has a tapered surface of about 35–55° with an upper end thereof being a slot (depending on the number of channels or grooves 40 in the glass substrate); the width of the opening 39 being from 0.2 to 4.0 mm. The channel or groove 40 may have a width of 0.1 to 40 mm, depth of 0.1 to 1.0 mm, and length of 5 to 40 mm. The glass substrate 32 may be provided with a number of grooves or channels 40 depending on the intended use. Similarly, the silicon substrate may be designed to include a plurality of spaced cutting edges to enable slicing plural specimens from the tissue as it passes over the cutters. The member 47 of FIG. 4 may have a thickness of 1.0 to 20 $\mu$m with space 48 having a width of 2–500 $\mu$m; and could also be constructed of polycrystalline silicon or silicon nitride. While it is preferred that the substrate or members 31 and 32 be constructed of silicon and glass, respectively, they both can be constructed of silicon, or one or both constructed of stainless steel, plastic, or aluminum, for example, providing the material is compatible with both the specimens being cut and treated as well as being compatible with the chemicals being used to treat the specimens.

It has thus been shown that the present invention provides a microfabricated biopsy/histology instrument which has several advantages over conventional procedures, including minimal specimen handling, smooth cutting edges with atomic sharpness capable of slicing very thin specimens (about 2 $\mu$m and greater), micro-liter volumes of chemicals for treating the specimens, low cost, disposable, fabrication process which renders sterile parts, and ease of use. This low cost and/or disposable instrument could replace the current expensive microtome and histology equipment currently used in clinics, hospitals, and research laboratories.

While particular embodiments of the cutter and instrument have been illustrated and/or described and particular materials, parameters, etc. have been described to exemplify and explain the principles of the invention, such are not intended to be limiting. Modifications and changes may become apparent to those skilled in the art, and it is intended that the invention be limited only by the scope of the appended claims.

What is claimed is:

1. In an instrument for tissue biopsy and analysis, the improvement comprising:
    at least one cutter member formed of silicon;
    said at least one silicon cutter member including a sharp cutting edge formed on an end of an opening extending therethrough;
    said at least one silicon cutter member additionally induding an indentation adjacent said sharp cutting edge having a depth which defines a thickness of a cut for tissue biopsy.

2. The improvement of claim 1, wherein said indentation extends from said sharp cutting edge to an outer edge of said cutter member, said outer edge of said cutter member defining a sharp cutting edge.

3. The improvement of claim 1, additionally including means in said opening for causing a specimen cut by said sharp cutting edge to lie flat in said instrument.

4. The improvement of claim 1, additionally including a glass member bonded to said silicon cutter member, said glass member having at least one channel adjacent said opening in said silicon member for analysis of a specimen cut by said sharp cutting edge.

5. The improvement of claim 1, wherein said opening defines a slot in said silicon member, said sharp cutting edge extending along one side of said slot, and with said indentation terminating at an opposite side of said slot.

6. The improvement of claim 5, wherein said slot between said sharp cutting edge and said indentation has a width of about 200–300 $\mu$m.

7. The improvement of claim 1, wherein said opening has a tapered configuration.

8. The improvement of claim 1, wherein said opening extends across only a portion of said silicon cutter member.

9. The improvement of claim 1, additionally including a glass member secured to said silicon cutter member at a surface opposite said indentation.

10. The improvement of claim 1, additionally including a glass member secured to said silicon cutter member, said glass member having at least one channel therein, said silicon cutter member having a second opening spaced from said first-mentioned opening, and said at least one channel in said glass member extending at least intermediate said openings in said silicon cutter member.

11. The improvement of claim 10, wherein each of said openings has a tapered configuration, and wherein the taper of each opening extends in opposite directions.

12. The improvement of claim 10, wherein said openings are located at opposite ends of said indentation in said silicon cutter member.

13. The improvement of claim 12, additionally including means for causing a specimen cut by said sharp cutting edge to lie flat in said instrument.

14. The improvement of claim 13, wherein said means comprises a member located at least partially in said first-mentioned opening in said silicon cutter member.

15. The improvement of claim 14, wherein said member includes a triangular shaped section positioned in said first-mentioned opening.

16. The improvement of claim 1, additionally including means for performing an optical analysis of a specimen cut by said cutting edge.

17. The improvement of claim 1, additionally including means for chemical treatment of a specimen cut by said cutting edge.

18. The improvement of claim 17, wherein said means includes a glass member secured to said silicon cutter member, said silicon cutter member includes an opening located in spaced relation to said first-mentioned opening, said glass member having at least one channel extending at least between said openings in said silicon cutter member, and said at least one channel containing a chemical.

19. The improvement of claim 18, wherein each of said openings in said silicon cutter member includes a tapered surface, and wherein said tapered surfaces of said openings taper in opposite directions.

* * * * *